United States Patent [19]
Verbeek

[11] Patent Number: 5,951,540
[45] Date of Patent: Sep. 14, 1999

[54] DEVICE AND METHOD FOR MOUNTING STENTS

[75] Inventor: Marcel A.E. Verbeek, Heerlen, Netherlands

[73] Assignee: Medtronic, Inc., Minneapolis, Minn.

[21] Appl. No.: 09/176,968

[22] Filed: Oct. 22, 1998

[51] Int. Cl.[6] .................................................. A61B 17/00
[52] U.S. Cl. ........................................................... 606/1
[58] Field of Search .............................. 606/1, 198, 194, 606/192, 195, 108; 623/1, 12

[56] References Cited

U.S. PATENT DOCUMENTS

| | | | |
|---|---|---|---|
| 3,637,447 | 1/1972 | Berger et al. | 156/180 |
| 3,862,482 | 1/1975 | Green | 29/203 DT |
| 4,515,550 | 5/1985 | Miller . | |
| 4,655,064 | 4/1987 | Hoback . | |
| 4,825,682 | 5/1989 | Orav et al. . | |
| 4,886,062 | 12/1989 | Wiktor . | |
| 5,138,864 | 8/1992 | Tarpill . | |
| 5,314,464 | 5/1994 | Knight et al. | 607/132 |
| 5,437,083 | 8/1995 | Williams et al. | 606/1 |
| 5,458,581 | 10/1995 | Hull | 604/248 |
| 5,476,506 | 12/1995 | Lunn | 623/1 |
| 5,571,540 | 11/1996 | Weyenberg et al. | 425/343 |
| 5,626,604 | 5/1997 | Cottone, Jr. | 606/198 |
| 5,630,830 | 5/1997 | Verbeek | 606/198 |
| 5,672,169 | 9/1997 | Verbeek | 606/1 |
| 5,681,346 | 10/1997 | Orth et al. | 606/198 |
| 5,693,066 | 12/1997 | Rupp et al. | 606/198 |
| 5,725,519 | 3/1998 | Penner et al. | 606/198 |
| 5,738,674 | 4/1998 | Williams et al. | 606/1 |
| 5,785,715 | 7/1998 | Schatz | 606/108 |
| 5,810,838 | 9/1998 | Solar | 606/108 |

*Primary Examiner*—Michael Buiz
*Assistant Examiner*—Kevin Truong
*Attorney, Agent, or Firm*—Kevin W. Raasch; Dianne Plunkett Latham; Harold R. Patton

[57] ABSTRACT

Crimping sleeves, devices and methods of crimping stents onto delivery devices are disclosed. The stent is located within a channel formed by a crimping sleeve including a set of crimping elements located about the channel. The crimping elements are connected by rotatable links such that compressing at least two opposing crimping elements together results in a reduction in the diameter of the channel and crimping of a stent located therein on a delivery device located therein.

20 Claims, 6 Drawing Sheets

DEVICE AND METHOD FOR MOUNTING STENTS

FIELD OF THE INVENTION

The present invention relates to methods and devices for mounting intravascular stent implants on delivery devices. More particularly, the present invention relates to methods and devices for crimping intravascular stent implants on delivery devices.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A typical stent is a cylindrically shaped wire formed device intended to act as a permanent prosthesis. A typical stent ranges from 5 mm to 50 mm in length. A stent is deployed in a body lumen from a radially compressed configuration into a radially expanded configuration which allows it to contact and support a body lumen. Many stents are designed to be expanded by the use of an expansion device within a body lumen. As a result, the stents are typically manufactured from materials that are plastically deformable. A plastically deformable stent can be implanted during a single angioplasty procedure by using a balloon catheter bearing a stent which has been crimped onto the balloon. The stent expands radially as the balloon is inflated, forcing the stent into contact with the interior of the body lumen thereby forming a supporting relationship with the vessel walls. After deployment, the biocompatible metal stent props open blocked coronary arteries, keeping them from reclosing after balloon angioplasty.

The problems facing those attempting to crimp stents onto expandable delivery devices, such as balloon catheters, are numerous. In some instances, the stents are manually crimped onto the delivery device using finger pressure or pliers. Such crimping can however, result in damage to the stent during handling prior to use as well as during the act of crimping because of the lack of control over the forces used during crimping. In either case, the damaged stents cannot be used. Furthermore, if the damage to the stent is not noticed, the stent may fail to perform as intended after deployment. In addition to damage to the stent itself before or during crimping, the crimping process can damage the delivery device if the forces applied during crimping are excessive.

Even if the stent and/or the delivery device are not damaged, other potential problems remain. For example, the stent may be non-uniformly crimped onto the delivery device which can cause problems during advancement of the stent to the desired location within a body lumen and/or during deployment of the stent.

Other problems include maintaining sterility of the stent. To assist with maintaining sterility, it is often preferred that the crimping devices be disposable such that they can be discarded after a single use. By disposing of the crimping device, the chance of cross-contamination originating with the crimping device itself can be eliminated.

Examples of crimping devices for stents are known, such as U.S. Pat. No. 5,626,604 to Cottone, Jr. which discloses a stent crimping device including a collet for radially crimping a stent onto a catheter. The collet includes radially compressible members that are compressed by use of sliding collet or a rotating collet.

U.S. Pat. No. 5,672,169 to Verbeek discloses a manual stent crimping device in which the stent is mounted between four corner blocks, with the upper and lower pairs of corner blocks being separated by compressible members. Compression of the upper and lower pairs of corner blocks forces the stent diameter to decrease, thereby crimping the stent onto a delivery device extending through the stent.

SUMMARY OF THE INVENTION

The present invention provides devices and methods of crimping stents onto delivery devices. In the preferred crimping devices, the stent is located within a channel formed by a crimping sleeve including a set of crimping elements located about the channel. The crimping elements are connected by rotatable links such that application of force to opposing crimping elements results in equal force being applied simultaneously by all of the crimping elements. As a result, the crimping device may be used to crimp stents onto delivery devices have a range of profiles. In addition, in some embodiments including a compression apparatus, the force used to crimp the stent can be easily and accurately controlled to provide increased uniformity in the crimping process.

The crimping device can be reusable and designed for operation in a manufacturing facility or closer to the point-of-use. It may be desirable that the crimping device act as a storage device for a stent before use in addition to crimping the stent onto a desired delivery device. If so provided, the crimping device and enclosed stent can be supplied as a single sterile unit with the crimping device being discarded after crimping.

In one aspect, the present invention provides a device for crimping a stent onto a catheter delivery system, the device including a generally tubular channel having a first, uncompressed diameter and a second, compressed diameter, the channel defining a longitudinal axis; a set of circumferentially-adjacent crimping elements located about the channel, each crimping element having a crimping surface defining a portion of the channel; a radial slot located between each pair of circumferentially-adjacent crimping elements; an offset slot located between each pair of circumferentially-adjacent crimping elements; a link located between the radial slot and the offset slot separating each pair of the circumferentially-adjacent crimping elements, the link having an inner end rotatably connected to one of the crimping elements in the pair of circumferentially-adjacent crimping elements and an outer end rotatably connected to the other crimping element in the pair of circumferentially-adjacent crimping elements; wherein motion of one crimping element inwardly towards the longitudinal axis causes all of the crimping elements in the set of crimping elements to move inwardly towards the channel, and further wherein the channel is compressed from the uncompressed diameter to the compressed diameter In other aspects, the crimping devices may include one or more of the following features or characteristics: the set of crimping elements may be biased outwardly from the tubular channel; the set of crimping elements may include four crimping elements; and the radial slot may include an inner portion extending radially away from the tubular channel with the link aligned with the inner portion of the radial slot.

The crimping device may also include a plurality of sets of crimping elements located along the channel and the plurality of the sets of crimping elements may be connected to each other, wherein inward motion of one of the sets of crimping elements causes inward motion of the adjacent set of crimping elements.

The device may further include a compression apparatus acting on at least one of the crimping elements, the compression apparatus capable of forcing the at least one crimping element inwardly towards the longitudinal axis. The compression apparatus may be capable of acting on two opposing crimping elements simultaneously, or it may be capable of acting on each of the crimping elements in the set of crimping elements simultaneously. The compression apparatus may include a compression chamber containing the set of crimping elements and compression fluid and it may also include a compressor. Alternatively, the compression apparatus may include at least one bladder for each of the crimping elements in the set of crimping elements. Further, the compression apparatus may include a pair of handles adapted for manual compression.

In another aspect, the present invention provides a combination comprising a stent and a crimping device, the crimping device including a generally tubular channel containing the stent, the channel having a first, uncompressed diameter and a second, compressed diameter, the channel defining a longitudinal axis; a set of circumferentially-adjacent crimping elements located about the channel, each crimping element having a crimping surface defining a portion of the channel; a radial slot located between each pair of circumferentially-adjacent crimping elements; an offset slot located between each pair of circumferentially-adjacent crimping elements; a link located between the radial slot and the offset slot separating each pair of the circumferentially-adjacent crimping elements, the link having an inner end rotatably connected to one of the crimping elements in the pair of circumferentially-adjacent crimping elements and an outer end rotatably connected to the other crimping element in the pair of circumferentially-adjacent crimping elements; wherein motion of one crimping element inwardly towards the longitudinal axis causes all of the crimping elements in the set of crimping elements to move inwardly towards the channel, and further wherein the channel and the stent are compressed from the uncompressed diameter to the compressed diameter.

In another aspect, the present invention provides a method of crimping a stent onto a delivery device by providing a crimping device containing a stent, the crimping device including a generally tubular channel containing the stent, the channel having a first, uncompressed diameter and a second, compressed diameter, the channel defining a longitudinal axis; a set of circumferentially-adjacent crimping elements located about the channel, each crimping element having a crimping surface defining a portion of the channel; a radial slot located between each pair of circumferentially-adjacent crimping elements; an offset slot located between each pair of circumferentially-adjacent crimping elements; a link located between the radial slot and the offset slot separating each pair of the circumferentially-adjacent crimping elements, the link having an inner end rotatably connected to one of the crimping elements in the pair of circumferentially-adjacent crimping elements and an outer end rotatably connected to the other crimping element in the pair of circumferentially-adjacent crimping elements; locating a delivery device within the channel, at least a portion of the delivery device being located within the stent; moving at least one of the crimping elements towards the longitudinal axis, wherein the channel and the stent are compressed against the delivery device.

As used in connection with the present invention, "crimping," refers to the plastic deformation caused by reducing the diameter of a stent from a first, uncompressed diameter to a second, compressed diameter;

"delivery device" refers to any device useful in the delivery of the stent to a desired location within a body lumen, the delivery device will typically be expandable with one specific example of a delivery device being a balloon catheter;

"longitudinal axis" refers to an imaginary line extending through the center of the tubular channel in which a stent is located during the crimping process;

"circumferentially-adjacent crimping elements" are crimping elements adjacent to each other when moving about the circumference of the crimping device;

"biased" in a direction means that the device will, in the absence of outside forces, assume a particular position.

These and other features and advantages of the present invention are discussed below with respect to various illustrative embodiments of the invention.

DETAILED DESCRIPTION OF ILLUSTRATIVE EMBODIMENTS

Figure 1:
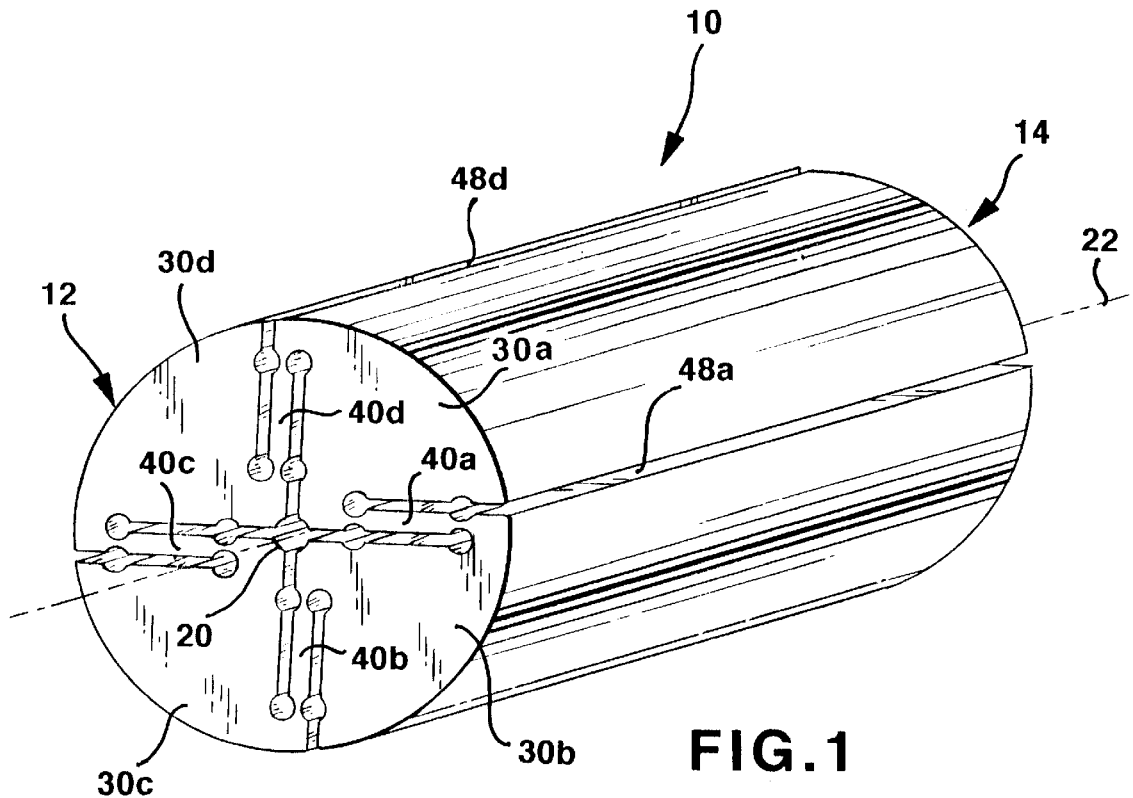
FIG. 1 is a perspective view of one crimping device according to the present invention.
Figure 2:
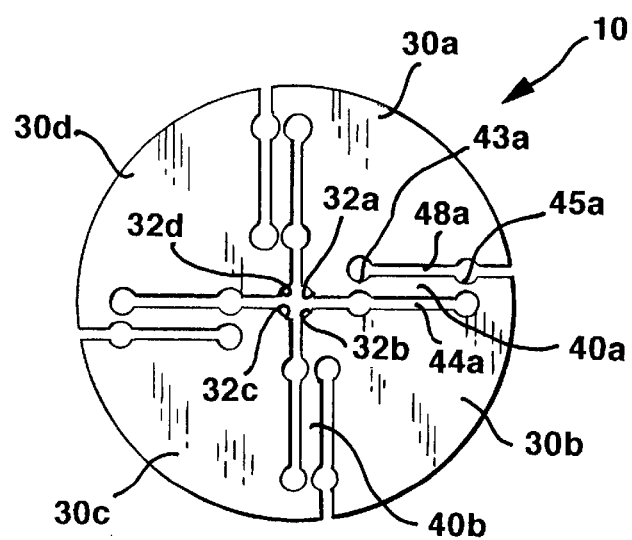
FIG. 2 is an end view of the device of FIG. 1.

The present invention provides a device useful for crimping stents onto a delivery device. FIGS. 1 and 2 illustrate one crimping sleeve 10 according to the present invention. The sleeve 10 includes a generally tubular channel 20 having an opening in the first end 12 of the sleeve 10. The channel 20 preferably defines a longitudinal axis 22 extending through the center of the channel 20 along its length.

It is preferred, but not required, that the tubular channel 20 extend completely through the sleeve 10 from the first end 12 to the second end 14. By extending the tubular channel completely through the sleeve 10, a catheter or other delivery device may be more easily located within the channel 20 during the crimping process.

As seen at the first end 12 of the sleeve 10, a set of circumferentially-adjacent crimping elements 30a, 30b, 30c and 30d (referred to generally as crimping elements 30 below) are located about the channel 20. Each of the crimping elements 30a–d includes a crimping surface 32a–d, respectively, that collectively define the channel 20 formed in crimping sleeve 10.

Referring now to the pair of circumferentially-adjacent crimping elements 30a and 30b, the connection between each pair of circumferentially-adjacent crimping elements 30 will now be described. A pair of slots 44a and 48a are formed in the sleeve 10. Radial slot 44a preferably extends radially from the tubular channel 20. One end of the radial slot 44a opens into the channel 20 and defines one edge of the crimping surface 32a and an opposing edge of crimping surface 32b. It is preferred that the radial slot 44a not extend to the outer perimeter of the sleeve 10.

Offset slot 48a is slightly offset circumferentially from the radial slot 44a and opens to the exterior of the sleeve 10 as seen in FIG. 1 (where both offset slots 48a and 48d are illustrated). The radial slot 44a and offset slot 48a form a link 40a that extends from the outer end of the radial slot 44a to the inner end of the offset slot 48a.

The link 40a is rotatably connected to crimping element 30b at inner end 43a and the outer end 45a is connected to crimping element 30a as indicated in FIG. 2. It is preferred that the connections between the link 40a and the crimping elements 30a/30b at both the inner end 43a and the outer end 45a be relatively flexible and the link 40a be relatively rigid and incompressible. It is further preferred that, in response to compressive forces on the crimping sleeve 10, the link 40a rotate about axes of rotation extending through the inner and outer ends 43a and 45a. The hinges 43a and 45a and their corresponding axes of rotation preferably extend parallel to the central longitudinal axis 22 extending through the tubular channel 20.

The crimping elements 30 are preferably biased outwardly in the position illustrated in FIGS. 1 and 2, i.e., biased outwardly such that the tubular channel 20 is in its first, uncompressed diameter. As the crimping sleeve 10 is compressed, the rotation of the link 40 about the inner and outer ends 43a and 45a allows the tangential width of the slots 44a and 48a to decrease. As illustrated in FIGS. 1 and 2, each of the crimping elements 30a–d includes a link 40a–d, respectively, along with the corresponding radial slot, offset slot, inner hinge, and outer hinge. As a result, during compression of the crimping sleeve 10, the tangential widths of the radial slots and the offset slots all typically decrease. By decreasing the width of the radial and offset slots, the diameter of the tubular channel 20 is decreased from a first, uncompressed diameter to a second, compressed diameter. Any stent located within the channel 20 also experiences that compression.

It is further preferred that, after the compressive forces are released, the crimping elements 30 move back outwardly from the longitudinal axis 22 to assist in removal of the stent and delivery device from the channel 20. In some instances the channel may return to its uncompressed diameter, but in other instances, some permanent deformation of the crimping sleeve 10 may have occurred during crimping.

Figure 3:
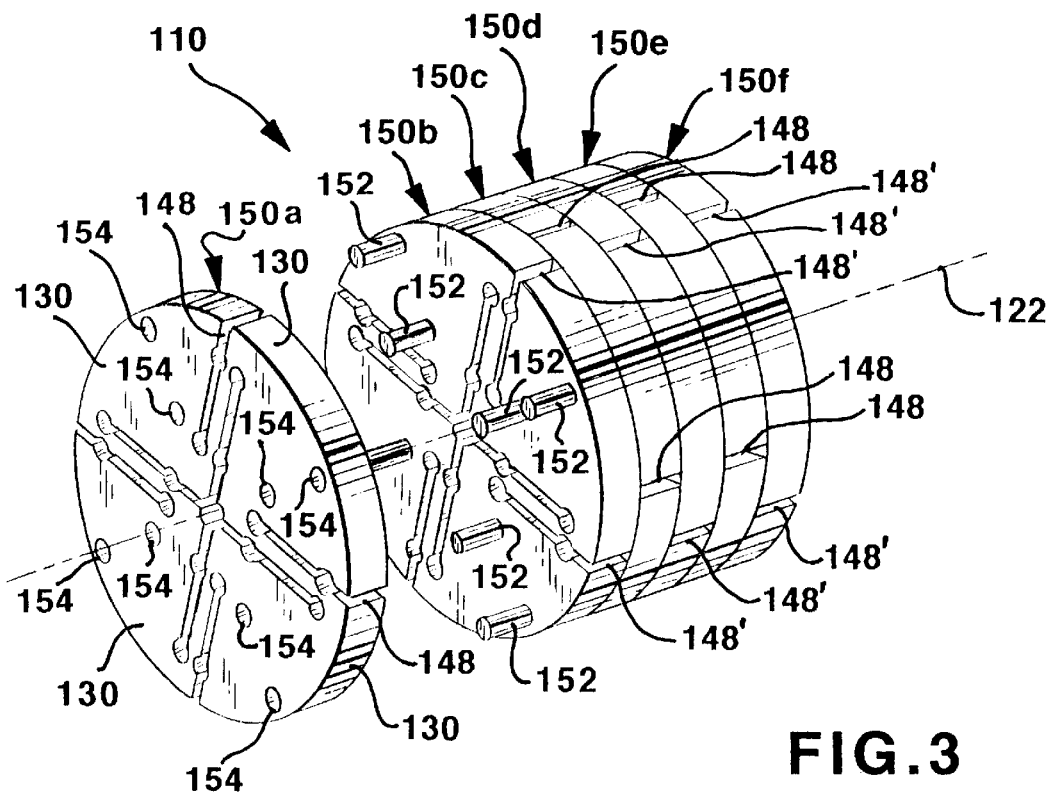
FIG. 3 is a partial exploded view of another crimping device according to the present invention.
Figure 4:
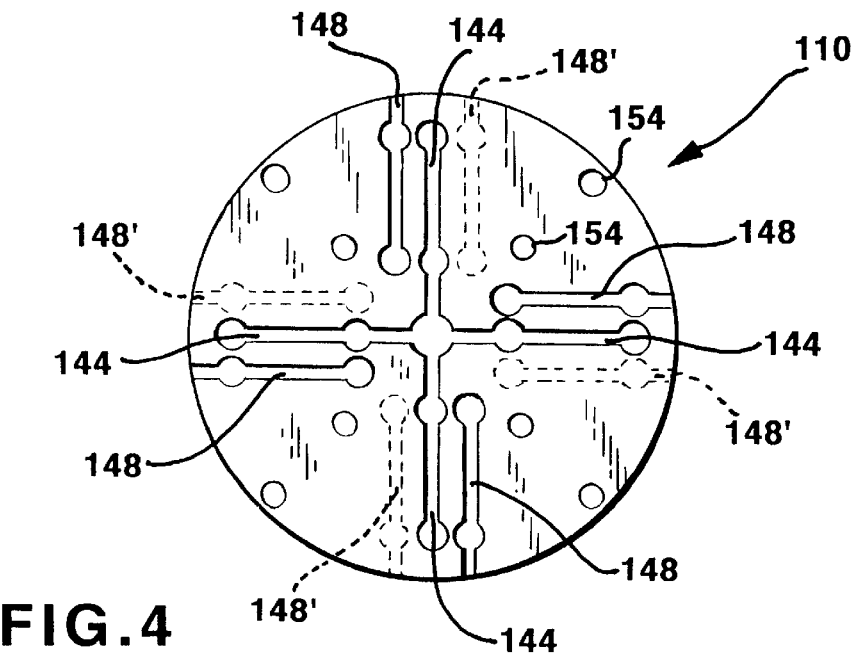
FIG. 4 is an end view of the crimping device of FIG. 3.

FIGS. 3 and 4 illustrate another crimping sleeve 110 according to the present invention. The crimping sleeve 110 includes a plurality of sets 150 of crimping elements 130a–d (collectively referred to as crimping elements 130). The sets 150 are aligned along a longitudinal axis 122, with the sets 150 collectively forming a tubular channel 120 in which a stent to be crimped can be located. The crimping elements 130 in each of the sets 150 are constructed similar to the crimping elements 30 discussed with respect to FIGS. 1 and 2 above, with the primary difference being the length or depth of the crimping elements 130.

Another difference in the crimping sleeve 110 is that the offset slots 148 in longitudinally adjacent sets 150 (i.e., sets 150 located next to each other along the longitudinal axis 122) are preferably located on alternating sides of their respective radial slots 144. This is illustrated in FIG. 3 where the offset slots 148 in successive sets of crimping elements are not aligned with each other, as well as in FIG. 4 where the offset slots 148' in the successive set 150 of crimping elements are depicted in broken lines.

Because alignment of the successive sets 150 of crimping elements 130 is desired, the illustrated sets 150 include alignment pins 152 and associated bores 154 that receive the pins 152 to maintain alignment of the crimping elements 130 between successive sets 150. It is preferred that each crimping element 130 include two or more alignment pins 152 and bores 154 to prevent rotation of the crimping elements 130 around the alignment pins 152 and bores 154 during the crimping process. It will be understood that many other mechanisms or techniques of maintaining alignment between the successive sets 150 of crimping elements 130 may be substituted for the illustrated alignment pins 152 and bores 154. The substitutions may include, but are not limited to shaping the mating surfaces of the sets 150 so that they nest in a particular orientation or bonding the sets 150 together during or after assembly (through the use of welds, adhesives, etc.).

It is preferred, but not required, that the alignment mechanism also transmit the compressive forces applied during crimping to the adjacent sets 150 of crimping elements 130. The pins 152 and bores 154 illustrated in FIG. 3 accomplish that function in addition to maintaining the alignment between crimping elements 130. By transmitting the compressive forces, the alignment pins 152 and bores 154 may provide more uniform compression along the longitudinal length of the crimping sleeve 110 even if the applied forces are not evenly distributed along that length.

Figure 5:
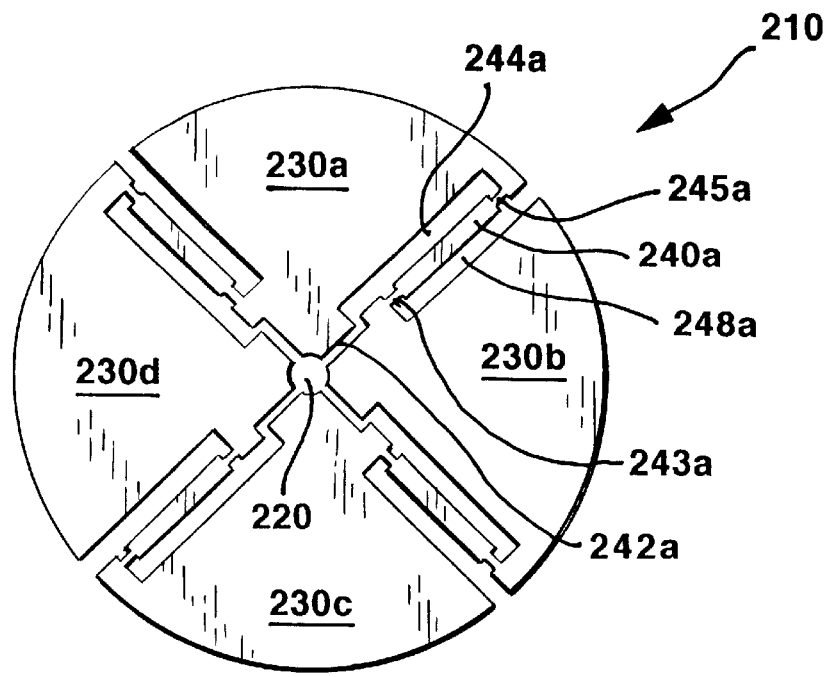
FIG. 5 is an end view of another crimping device according to the present invention with the tubular channel in the uncompressed diameter.

Another crimping sleeve according to present invention is illustrated in FIG. 5. The sleeve 210 also includes a plurality (preferably four) crimping elements 230a–d (collectively referred to as crimping elements 230) located about a tubular channel 220. The interconnection of the crimping elements 230 will now be described with specific reference to crimping element 230a, although t will be understood that the construction is the same for each of the crimping elements 230.

Crimping element 230a is separated from its circumferentially-adjacent crimping elements 230b and 230d by a radial slot 244a and an offset slot 248a. The radial slot 244a opens into the channel 220 and the offset slot 248a opens to the exterior of the crimping sleeve 210.

A relatively rigid link 240a is located between the radial slot 244a and the offset slot 248a. It is preferred that the link 240a be radially aligned with the inner portion 242a of the radial slot 244a as seen in FIG. 5. The link 240a is connected to crimping element 230a at its outer end 245a and is connected to crimping element 230b at its inner end 243a. The connections of the link 240a to crimping elements 230a and 230b preferably allow the link 240a to rotate about axes extending through the connections 243a and 245a (those axes extend out of the page in the view illustrated in FIG. 5). In other words, the connections 243a and 245a function as hinges, allowing the relatively rigid links (such as link 240a) to rotate while the crimping elements 230 are moving inward to compress a stent.

During compression of the crimping sleeve, movement of the opposing crimping elements 230a and 230c towards each other (see FIG. 6) causes corresponding inward motion of the intervening crimping element 230b and 230d because of the hinged or rotatable connections between the crimping elements 230 provided by the links as discussed above. In addition, the forces applied to the opposing crimping elements 230a and 230c is also distributed by the hinged link connections.

Figure 6:
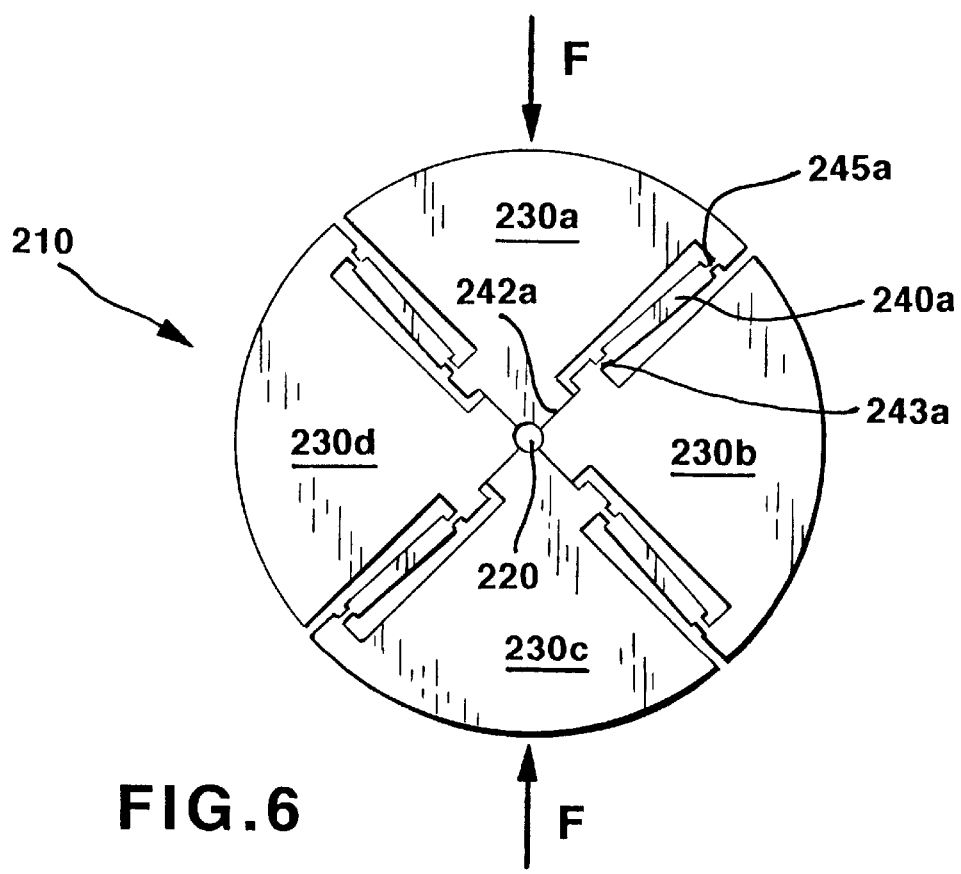
FIG. 6 is an end view of the crimping device of FIG. 5 with the tubular channel in the compressed diameter.

The results of the rotation of the links includes the narrowing of the inner portion 242a of the radial slot 244a which, in FIG. 6, is depicted as being entirely closed. It will be understood that the inner portions of the radial slots may, in some instances, not be entirely closed during crimping. Furthermore, it should be understood that the inner portions of the radial slots may not close uniformly, i.e., one or more of the slots may have different tangential widths as the crimping sleeve 210 conforms to the profile of the delivery device on which the stent is being mounted.

One advantage of the crimping sleeve 210 over the other embodiments described above is that the tangential width of the inner portion 242a of the radial slot 244a can typically be narrower that the corresponding width of the radial slots 44/144 in the crimping sleeves 10/110. That narrower width assists in reducing the likelihood that struts on a stent inserted into the tubular channel 220 can be caught in the inner portion 242a of the radial slot 242a and damaged during crimping.

Figure 7:
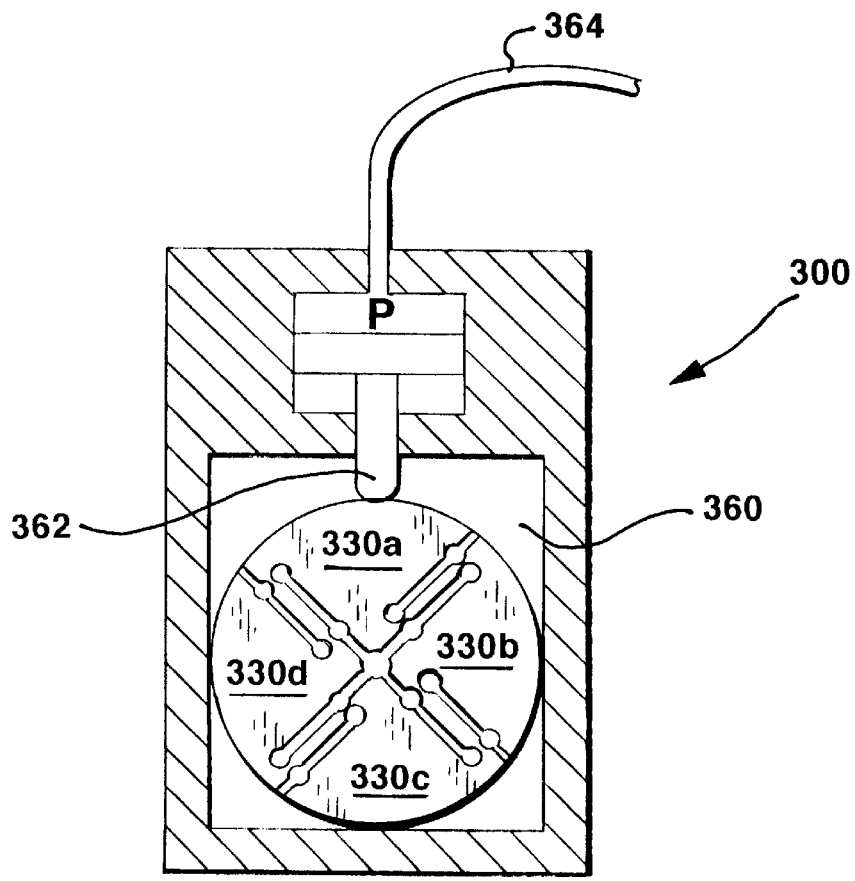
FIG. 7 is an end view of another crimping device including a compression apparatus.
Figure 8:
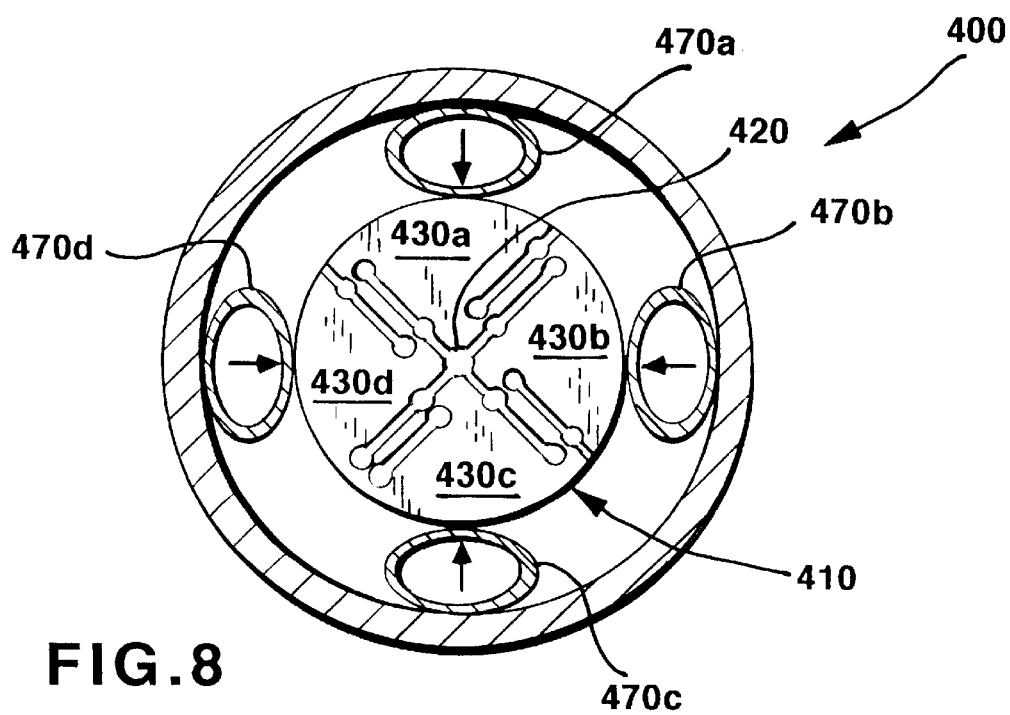
FIG. 8 is an end view of another crimping device including another compression apparatus.
Figure 9:
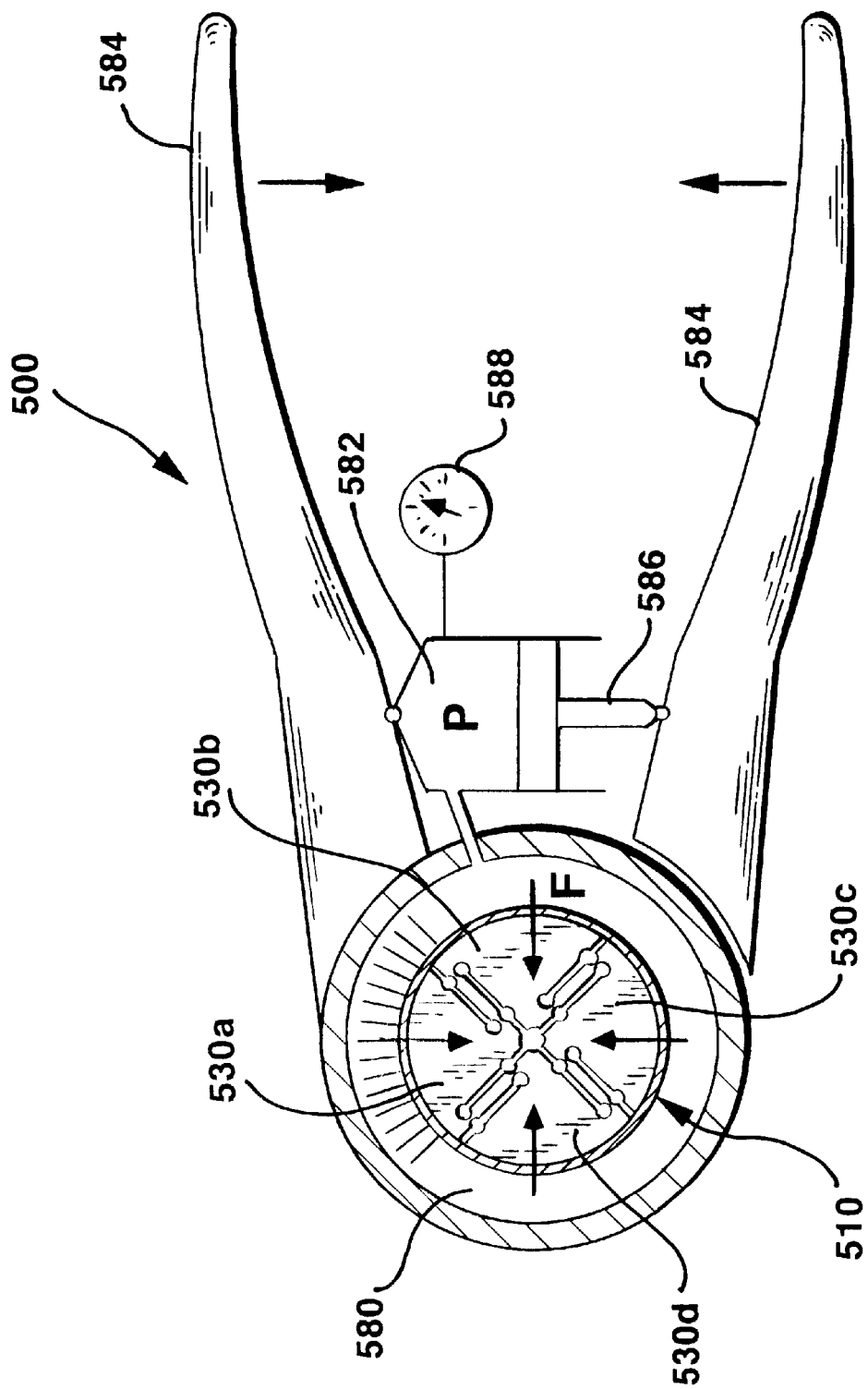
FIG. 9 is a partial cross-sectional view of another crimping device including another compression apparatus.

In addition to the crimping devices described above, the crimping devices according to the present invention may also include a compression apparatus used in compressing the crimping sleeve. FIGS. 7–9 depict various illustrative crimping devices including compression apparatus in accordance with the present invention. Although the crimping devices described above can be compressed manually (using finger pressure), it may be desirable to use a compression apparatus that can allow for more precise control of the crimping forces. Control over the crimping forces can result in more reliable crimping of stents on delivery devices.

FIG. 7 illustrates one crimping device 300 including a compression apparatus in the form of a chamber 360 and plunger 362 with a crimping sleeve 310 located within the chamber 360. The plunger 362 can be extended downward, causing the opposing crimping elements 330a–d in the sleeve 310 to move towards each other, thereby reducing the diameter of the tubular channel 320. It is preferred that the plunger 362 be driven hydraulically by fluid pressure supplied through line 364, although alternative techniques of providing for motion of the plunger 362 are also envisioned. One alternative could include, e.g., an electromagnetically driven plunger. Regardless of the source of the driving force, it is preferred that it be controllable with respect to magnitude.

FIG. 8 illustrates another crimping device 400 including an alternative compression apparatus including a series of bladders 470a–d (collectively referred to as bladders 470) located about a crimping sleeve 410. Each bladder 470 is located between an outer wall 472 and one of the crimping elements 430a–d. As a result, inflation of the bladders 470 by a fluid source (not shown) causes the crimping elements 430a–d to move inwardly, compressing the tubular channel 420. One advantage of the compression apparatus illustrated in FIG. 8 is that the inflation pressures of the bladders 470 can be balanced such that the force on each of the crimping elements 430a–d is also balanced. This force-balancing may improve the uniformity of the crimping process.

FIG. 9 illustrates another crimping device 500 including a compression apparatus in which the crimping sleeve 510 including crimping elements 530a–d is located within a pressure chamber 580. The compression apparatus includes a pressure source 582 in fluid communication with the pressure chamber 580. Because the crimping sleeve 510 is located within a single chamber 580, the forces applied to each of the crimping elements 530a–d of the sleeve 510 will be balanced.

FIG. 9 also depicts one actuator for providing the pressure from source 582 in the form of a pair of handles 584 that can be moved together, causing a plunger 586 to act on the source 582. Because this compression apparatus includes manual input, it may be preferred to supply a gauge 588 as shown to allow monitoring of the fluid pressure and, as a result, the forces applied to the crimping sleeve 510.

Figure 10:
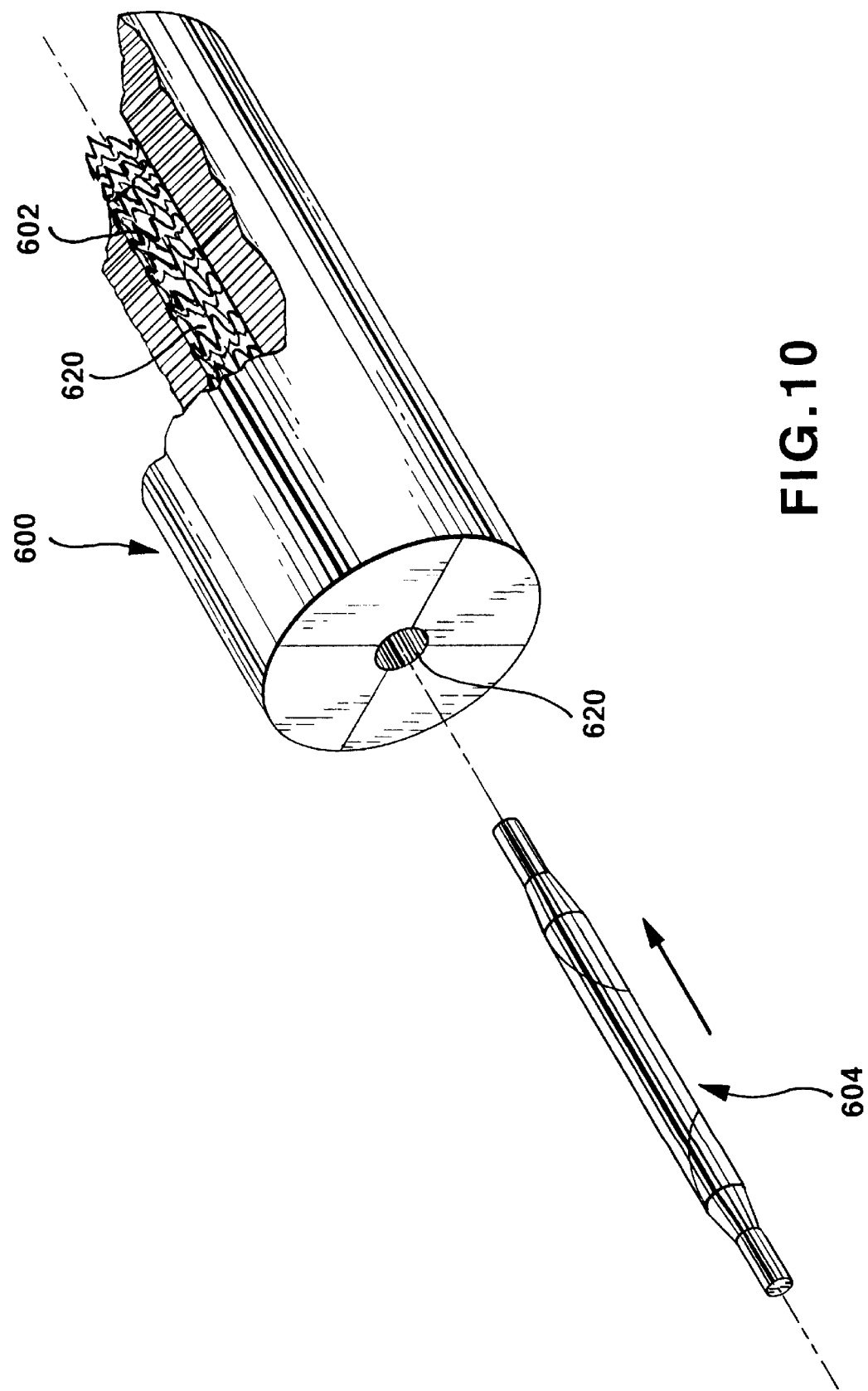
FIG. 10 is a perspective view of another crimping device including a stent and delivery device on which the stent is to be mounted.

FIG. 10 illustrates one crimping device 600 in which a portion of the device is removed to expose the stent 602 located within the tubular channel 620. In some instances, it may be desirable to manufacture the crimping device 600 separate from the stent 602 and locate the stent 602 within the channel 620 of the crimping device 600 after manufacturing. In other instances, it may be possible to manufacture the crimping device 600 around the stent 602 by, e.g., insert injection molding or other suitable techniques.

Regardless of how manufactured, the crimping device 600 with the stent 602 located within channel 620 are then provided for insertion of a delivery device 604 into the channel 620. Because the stent 602 is already located within the channel 620, the delivery device 604 is also located within the stent 602 when in channel 620. To assist in positioning of the delivery device 604, it may be desirable to provide a crimping device 600 that is translucent or transparent such that the position of the delivery device relative to the stent 602 can be visually monitored.

After the delivery device 604 is in the proper position within the stent 602 and channel 620, the crimping device 600 can be compressed as described above to crimp the stent 602 onto the outer surface of the delivery device 604. Following crimping, the delivery device 604, with attached stent 602, can be removed. Where the crimping device is reusable, another stent may be loaded into the channel 620 for crimping onto another delivery device (with intervening sterilization where required). Alternatively, the crimping device 600 may be disposable and, as a result, it may be discarded after use.

All of the crimping devices described above can be manufactured by known methods using any suitable materials. Regardless of the actual materials used, it may be preferred that at least the crimping sleeves be constructed of materials capable of withstanding sterilization. With respect to the crimping sleeves themselves, it may be desirable to manufactured them by injection molding, extrusion, or other methods.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10/110/210/410/510 | Crimping Sleeve |
| 12 | First End of Crimping Sleeve 10 |
| 14 | Second End of Crimping Sleeve 10 |
| 20/220/420/620 | Tubular Channel |
| 22/122 | Longitudinal Axis of Tubular Channel |
| 30/130/230/430/530 | Crimping Element |
| 32 | Crimping Surface of Crimping Element |
| 40/240 | Link |
| 242 | Inner Portion of Radial Slot 244 |
| 43/243 | Inner End of Link |
| 44/144/244 | Radial Slot |
| 45/245 | Outer End of Link |
| 48/148/248 | Offset Slot |
| 150 | Set of Crimping Elements |
| 152 | Alignment Pins |
| 154 | Alignment Bores |
| 300/400/500/600 | Crimping Device |
| 360 | Crimping Chamber |
| 362 | Plunger |
| 470 | Bladder |
| 580 | Pressure Chamber |
| 582 | Pressure Source |
| 584 | Handle |
| 586 | Plunger |
| 588 | Pressure Gauge |
| 602 | Stent |
| 604 | Delivery Device |

What is claimed is:

1. A device for crimping a stent onto a catheter delivery system, the device comprising:
    a generally tubular channel having a first, uncompressed diameter and a second, compressed diameter, the channel defining a longitudinal axis;
    a set of circumferentially-adjacent crimping elements located about the channel, each crimping element having a crimping surface defining a portion of the channel;
    a radial slot located between each pair of circumferentially-adjacent crimping elements;
    an offset slot located between each pair of circumferentially-adjacent crimping elements;
    a link located between the radial slot and the offset slot separating each pair of the circumferentially-adjacent crimping elements, the link having an inner end rotatably connected to one of the crimping elements in the pair of circumferentially-adjacent crimping elements and an outer end rotatably connected to the other crimping element in the pair of circumferentially-adjacent crimping elements;
    wherein motion of one crimping element inwardly towards the longitudinal axis causes all of the crimping elements in the set of crimping elements to move inwardly towards the channel, and further wherein the channel is compressed from the uncompressed diameter to the compressed diameter.

2. A device according to claim 1, wherein the set of crimping elements is biased outwardly from the tubular channel.

3. A device according to claim 1, wherein the set of crimping elements includes four crimping elements.

4. A device according to claim 1, wherein the radial slot comprises an inner portion extending radially away from the tubular channel and further wherein the link is aligned with the inner portion of the radial slot.

5. A device according to claim 1, further comprising a plurality of sets of crimping elements located along the channel.

6. A device according to claim 5, wherein the plurality of the sets of crimping elements are connected to each other, wherein inward motion of one of the sets of crimping elements causes inward motion of the adjacent set of crimping elements.

7. A device according to claim 1, further comprising a compression apparatus acting on at least one of the crimping elements, the compression apparatus capable of forcing the at least one crimping element inwardly towards the longitudinal axis.

8. A device according to claim 7, wherein the compression apparatus acts on two opposing crimping elements simultaneously.

9. A device according to claim 7, wherein the compression apparatus acts on each of the crimping elements in the set of crimping elements simultaneously.

10. A device according to claim 7, wherein the compression apparatus comprises a compression chamber containing the set of crimping elements and compression fluid.

11. A device according to claim 10, wherein the compression apparatus comprises a compressor.

12. A device according to claim 7, wherein the compression apparatus comprises at least one bladder for each of the crimping elements in the set of crimping elements.

13. A device according to claim 7, wherein the compression apparatus includes a pair of handles adapted for manual compression.

14. A combination comprising a stent and a crimping device, the crimping device comprising:
    a generally tubular channel containing the stent, the channel having a first, uncompressed diameter and a second, compressed diameter, the channel defining a longitudinal axis;
    a set of circumferentially-adjacent crimping elements located about the channel, each crimping element having a crimping surface defining a portion of the channel;
    a radial slot located between each pair of circumferentially-adjacent crimping elements;
    an offset slot located between each pair of circumferentially-adjacent crimping elements;
    a link located between the radial slot and the offset slot separating each pair of the circumferentially-adjacent crimping elements, the link having an inner end rotatably connected to one of the crimping elements in the pair of circumferentially-adjacent crimping elements and an outer end rotatably connected to the other crimping element in the pair of circumferentially adjacent crimping elements;
    wherein motion of one crimping element inwardly towards the longitudinal axis causes all of the crimping elements in the set of crimping elements to move inwardly towards the channel, and further wherein the channel and the stent are compressed from the uncompressed diameter to the compressed diameter.

15. A combination according to claim 14, further comprising a compression apparatus acting on at least one of the crimping elements, the compression apparatus capable of forcing the at least one crimping element inwardly towards the longitudinal axis.

16. A method of crimping a stent onto a delivery device, the comprising:

providing a crimping device containing a stent, the crimping device comprising:

a generally tubular channel containing the stent, the channel having a first, uncompressed diameter and a second, compressed diameter, the channel defining a longitudinal axis;

a set of circumferentially-adjacent crimping elements located about the channel, each crimping element having a crimping surface defining a portion of the channel;

a radial slot located between each pair of circumferentially-adjacent crimping elements, the radial slot opening into the channel;

an offset slot located between each pair of circumferentially-adjacent crimping elements, the offset slot opening to an exterior of the crimping device;

a link located between the radial slot and the offset slot separating each pair of the circumferentially-adjacent crimping elements, the link having an inner end rotatably connected to one of the crimping elements in the pair of circumferentially-adjacent crimping elements and an outer end rotatably connected to the other crimping element in the pair of circumferentially-adjacent crimping elements;

locating a delivery device within the channel, at least a portion of the delivery device being located within the stent;

moving at least one of the crimping elements towards the longitudinal axis, wherein the channel and the stent are compressed against the delivery device.

17. A method according to claim 16, wherein the at least one crimping element is moved by compressing two of the crimping elements on opposing sides of the channel towards each other.

18. A method according to claim 16, wherein moving at least one of the crimping elements causes all of the crimping elements to move towards the longitudinal axis.

19. A method according to claim 16, further comprising providing a compression apparatus, the compression apparatus acting to move at least one crimping element.

20. A method according to claim 16, wherein the crimping elements are biased outwardly from the longitudinal axis.

* * * * *